(12) United States Patent
Ishida (10) Patent No.: US 11,324,623 B2
(45) Date of Patent: May 10, 2022

(54) BODY TRUNK SUPPORTER AND WEAR PROVIDED WITH SAME

(71) Applicant: POJI CO., LTD., Miki (JP)

(72) Inventor: Yoshinobu Ishida, Toyonaka (JP)

(73) Assignee: POJI CO., LTD., Miki (JP)

( * ) Notice: Subject to any disclaimer, the term of this patent is extended or adjusted under 35 U.S.C. 154(b) by 413 days.

(21) Appl. No.: 16/464,727

(22) PCT Filed: Nov. 29, 2017

(86) PCT No.: PCT/JP2017/042849
§ 371 (c)(1),
(2) Date: May 29, 2019

(87) PCT Pub. No.: WO2018/101344
PCT Pub. Date: Jun. 7, 2018

(65) Prior Publication Data
US 2019/0343690 A1 Nov. 14, 2019

(30) Foreign Application Priority Data
Nov. 30, 2016 (JP) .............................. JP2016-232978

(51) Int. Cl.
*A61F 5/02* (2006.01)
*A41D 13/00* (2006.01)
(Continued)

(52) U.S. Cl.
CPC .......... *A61F 5/028* (2013.01); *A41D 13/0015* (2013.01); *A61F 5/02* (2013.01);
(Continued)

(58) Field of Classification Search
CPC .......... A61F 13/14; A61F 13/148; A61F 5/02; A61F 5/26; A61F 5/028; A61F 5/03;
(Continued)

(56) References Cited

U.S. PATENT DOCUMENTS 4,470,417 A * 9/1984 Gruber .................... A61F 5/028
128/DIG. 15
7,871,388 B2 * 1/2011 Brown ...................... A61F 5/34
602/19
(Continued)

FOREIGN PATENT DOCUMENTS

DE 112014003641 T5 4/2016
JP 2001-017456 A 1/2001
(Continued)

OTHER PUBLICATIONS

European Patent Office, Supplementary European Search Report issued in corresponding Application No. 17875699.5 dated Jul. 13, 2020.
(Continued)

*Primary Examiner* — Keri J Nelson
(74) *Attorney, Agent, or Firm* — Stites & Harbison, PLLC; Jeffrey A. Haeberlin; Gary N. Stewart (57) ABSTRACT

A body trunk supporter provided with: a belt-like lower band section that is adapted to be wrapped around and positioned at the pelvis of a user; an X-shaped stretchable middle band section that has a pair of lower end parts joined to the lower band section and that presses areas of the lumbar region of the user; and a pair of upper band sections that are jointed to a pair of upper end parts of the middle band section and that are adapted to be wrapped around and positioned at the chest of the user, wherein the pair of lower end parts of the middle band section are configured to be joined to areas ranging from positions that are immediately lateral to the pelvis of the user to adjacent anterior positions thereof in the lower band section; and the pair of upper band sections are configured to be separated from each other and to extend in bilaterally opposite directions in an unfolded state, and are con-
(Continued)

figured to be wrapped around and positioned near fifth to tenth ribs of the chest of the user.

7 Claims, 9 Drawing Sheets

(51) Int. Cl.
  *A61F 13/14* (2006.01)
  *A41B 9/12* (2006.01)
  *A41D 13/05* (2006.01)

(52) U.S. Cl.
  CPC .............. *A61F 13/148* (2013.01); *A41B 9/12* (2013.01); *A41D 13/0531* (2013.01)

(58) Field of Classification Search
  CPC . A61F 5/026; A41D 13/0015; A41D 13/0531; A41D 13/00; A41D 13/05; A41D 13/0525; A41D 2400/32; A41B 9/12
  See application file for complete search history.

(56) References Cited

U.S. PATENT DOCUMENTS

| 10,413,438 B1* | 9/2019 | Vangeloff ................. A61F 5/30 |
| 2014/0276308 A1 | 9/2014 | DiAngelo et al. |
| 2014/0343472 A1 | 11/2014 | Paulos et al. |

FOREIGN PATENT DOCUMENTS

| JP | 2001-218779 A | 8/2001 |
| JP | 2002-177309 A | 6/2002 |
| JP | 3102373 U | 7/2004 |
| JP | 2008-279065 A | 11/2008 |
| JP | 2010-104707 A | 5/2010 |
| JP | 4834175 B1 | 12/2011 |
| JP | 2013-085695 A | 5/2013 |
| JP | 2015-139605 A | 8/2015 |
| JP | 3204454 U | 6/2016 |
| WO | 2015/021395 A1 | 2/2015 |

OTHER PUBLICATIONS

Japan Patent Office, International Search Report issued in corresponding Application No. PCT/JP2017/042849, dated Jan. 16, 2018.

* cited by examiner

BODY TRUNK SUPPORTER AND WEAR PROVIDED WITH SAME

TECHNICAL FIELD

The present invention relates to a body trunk supporter and a wear provided with the same.

BACKGROUND ART

Patent Literature 1 proposes a back supporter used to alleviate or prevent low back pain. This back supporter has a belt lower portion and a belt upper portion, these portions being parallel to each other; and the back supporter comprises a stretchable belt body where center portions of the above-described lower and upper portions in a longitudinal direction are connected to each other; and ends of the belt lower portion and ends of the belt upper portion are respectively provided with hook-and-loop fasteners, each of the fasteners comprising a hook fiber surface portion and a loop fiber surface portion.

This back supporter seems to be capable of efficiently increasing abdominal pressure, and relieving or preventing low back pain, through the following procedure: The center portions at the belt body are placed on the lumbar of a user; the ends of the belt lower portion and the ends of the belt upper portion are wrapped toward the abdomen side; the hook fiber surface portions and the loop fiber surface portions of the fasteners are overlapped with and surface-contact fastened to each other; and the belt body is adapted to be wrapped around the entire circumference of the abdomen and fixated.

CITATION LIST

Patent Literature

[PTL 1]
Japanese Unexamined Patent Application Publication No. 2015-139605

SUMMARY OF INVENTION

Technical Problems

A back supporter, such as the one of PTL 1, that is wrapped around the entire circumference of the abdomen of a wearer cannot exert its effects when the supporter is loosely wrapped around the abdomen; therefore, the supporter requires some degree of tightness. For that reason, the back supporter compresses the wearer's abdomen and thus compresses the internal organs such as the stomach and the intestines as well. Such a back supporter makes it difficult for the wearer to eat and/or drink while wearing the back supporter; therefore, it is necessary for the wearer to take off the back supporter at mealtimes; and it is necessary to refrain from wearing the back supporter for a certain time after the meal.

If the user wears the back supporter for a long time that compresses the abdomen, the supporter is likely to cause various harmful effects to the human body such as breathing problems (breathing difficulty) caused by hindering the user from breathing with the lower half of the lungs and increasing burdens on the upper half of the lungs; digestive system problems (digesting difficulty), constipation, etc. caused by holding down the internal organs, such as the stomach, the kidneys, and the intestines, and developing splanchnoptosia; and cardiovascular problems caused by compressing veins that let blood pass from the lower body to the heart.

The traditional back supporter as described above had the structure that alleviates pain by compressing and fixating the lumbar and the abdomen, by limiting motions of the back muscles and the abdominal muscles, and by not using muscle strength as much as possible. In this case, there were harmful effects such as demerits such that the user feels uncomfortable due to the compressed abdomen; the blood flow is obstructed when the back support is used for a long time; and the muscles themselves are weakened because the muscle motions are limited, and the pain increases more when the supporter is unfastened.

The muscles contract at some parts of the painful back (for example, acute lower back pain), causing distortions of the body; however, the distortions of the body could not be corrected by compressing and fixating the lumbar and the abdomen.

In view of such problems above, the present invention has an object of providing a body trunk supporter and a wear provided with the supporter, the body trunk supporter being able to be worn without compressing and fixating the lumbar and the abdomen, and making it easy to keep the spinal column in a correct (or proper) S-shaped curve.

Solutions to Problems

The present invention provides a body trunk supporter provided with: a belt-like lower band section that is adapted to be wrapped around and positioned at the pelvis of a user; an X-shaped stretchable middle band section that has a pair of lower end parts joined to the lower band section and that is adapted to press areas of the lumbar region of the user; and a pair of upper band sections that are jointed to a pair of upper end parts of the middle band section and that are adapted to be wrapped around and positioned at the chest of the user,
wherein the pair of lower end parts of the middle band section are configured to be joined to areas ranging from positions that are immediately lateral to the pelvis of the user to adjacent anterior positions thereof in the lower band section; and
the pair of upper band sections are configured to be separated from each other and to extend in bilaterally opposite directions in an unfolded state, and are configured to be wrapped around and positioned near fifth to tenth ribs of the chest of the user.

Another aspect of the present invention is to provide a wear comprising a wear body and the above-described body trunk supporter provided on an outer surface of the wear body.

Advantageous Effects of Invention

The body trunk supporter of the present invention is worn through a procedure as follows: The lower band section is positioned around the user's pelvis; the pair of upper band sections are positioned at the chest; the cross portion of the X-shaped middle band section pushes the lumbar region forward; and the chest is drawn backward by the pair of upper band sections. As a result, the user's spinal column is corrected to the normal (or proper) S-shaped curve; and this enables the alleviation and the prevention of the lower back pain. In this instance, if the pair of upper band sections are connected with each other on the user's back side, the force of the pair of upper band sections that pulls the chest backward decreases, making it difficult to correct the spinal column to the normal S-shaped curve; on the other hand, the body trunk supporter of the present invention can effectively correct the spinal column to the normal S-shaped curve by interacting (or in a synergistic manner) with the middle band section because the pair of upper band sections are separated from each other.

In addition, the body trunk supporter of the present invention that does not compress the user's abdomen when being worn has the following advantages as examples, and can be safely and comfortably worn in daily life: The various harmful effects (damages), which are caused by compressing the abdomen, to the human body are not likely to occur, such as breathing problems, digestive system problems, and cardiovascular problems; the user wearing the supporter does not suffer from the squeezed abdomen while eating and drinking; and the body trunk supporter enables the user to carry out desk work comfortably in a sitting posture or to easily (or effortlessly) practice mild bending exercise.

The user can also enjoy the above-described advantageous effects by wearing the wear provided with the body trunk supporter of the present invention.

DESCRIPTION OF EMBODIMENTS

A body trunk supporter of the present invention comprises: a belt-like lower band section that is adapted to be wrapped around and positioned at the pelvis of a user; an X-shaped stretchable middle band section that has a pair of lower end parts joined to the lower band section and that is adapted to press areas of the lumbar region of the user; and a pair of upper band sections that are jointed to a pair of upper end parts of the middle band section and that are adapted to be wrapped around and positioned at the chest of the user, wherein the pair of lower end parts of the middle band section are configured to be joined to areas ranging from positions that are immediately lateral to the pelvis of the user to adjacent anterior positions thereof in the lower band section; and the pair of upper band sections are separated from each other and extend in bilaterally opposite directions in an unfolded state, and are configured to be wrapped around and positioned near fifth to tenth ribs of the chest of the user.

Namely, the body trunk supporter of the present invention is configured such that a pair of bands (to be described below) of the X-shaped stretchable middle band section are respectively placed from a lower part of the right anterior chest to the left anterior pelvis and from a lower part of the left anterior chest to the right anterior pelvis of the user; and an intersecting part of the pair of bands is placed near the lumbar vertebrae of the user. The body trunk supporter of the present invention configured as above is capable of supporting erector spinae muscles of the lumbar region of the user, with the result that muscle tension of the lumbar region can be eased; right and left distortions of the body can be corrected; and/or the spinal column can be kept in a correct S-shaped curve.

The body trunk supporter of the present invention may have the following structures, and may be formed by any combinations of these structures.

(1) The lower band section may comprise: a lower loop fiber surface portion of a lower surface fastener portion that is provided at one end of the lower band section; and a lower hook fiber surface potion of a lower surface fastener portion that is provided at the other end of the lower band section and that is connectable with the lower loop fiber surface portion by way of surface contact;

wherein one of the pair of upper band sections has an upper loop fiber surface potion of an upper surface fastener portion provided at one end of the upper band section; and the other one of the pair of upper band sections has an upper hook fiber surface potion of an upper surface fastener portion that is provided at one end of the upper band section and that is connectable with the upper loop fiber surface portion by way of surface contact.

In this way, the body trunk supporter can be put on or put off easily and conveniently, and also can fit to different physical frames of users.

Instead of the upper and lower surface fastener portions, the present invention may have the following structure as an example: Both ends of the lower band section and each end of the pair of upper band sections may have strings sewn thereto; and the strings may be tied to each other so as to fasten the lower band section and the pair of upper band sections to the body trunk; however, the upper and lower surface fastener portions are preferable in consideration of easiness of putting on or putting off the supporter and compatibility with the differences in the physiques.

(2) The lower band section may have stretchability.

In this way, the stretchable lower band section tightens the circumference of the pelvis of the user who wears the body trunk supporter; and the lower band section is not likely to slip off the circumference of the pelvis even when the user gets in motion such as walking or mild exercises. Moreover, the abdomen of the user wearing the body trunk supporter is not compressed; and the lower abdomen of the user can be firmly supported by the stretchable lower band section; therefore, this makes it possible to effectively prevent splanchnoptosia caused by wearing a conventional back supporter.

(3) The middle band section may comprise: a pair of rubber band members having intersection part of X shape; and a cloth retention member provided at the intersection part of the pair of rubber band members and having a pair of loop parts through which the rubber band members are respectively inserted.

With such as a configuration, the pair of rubber band members are prevented by the retention member from being loosened from each other, so that when the body trunk supporter is worn, the pair of upper band sections can be easily wrapped and worn (wound) around and toward the chest side; and the intersecting part of the middle band section is likely to fit to the user's lumbar with use of the retention member.

(4) The retention member may comprise: a tube part having one of the loop parts through which one of the pair of rubber band members is inserted; a band loop part provided on an outer surface of the tube part and having the other of loop parts through which the other of the pair of rubber band members is inserted; and a pocket provided on an outer surface of the tube part or on an outer surface of the band loop part.

With such a configuration, the pocket can contain a disposable body warmer; and the user can wear the body trunk supporter in such a way that the pocket side touches the user, thereby warming the user's lumber region with the warmed disposable body warmer. This can facilitate (or improve) blood circulation around the lumbar region of the user and can relieve (or alleviate) or prevent back pain more effectively.

In the following, Embodiments of body trunk supporters of the present invention will be described through the use of drawings.

Embodiment 1

Figure 1:
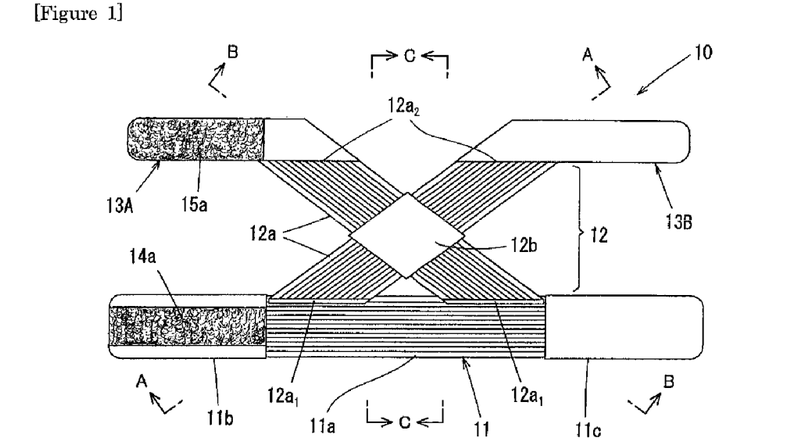
FIG. 1 illustrates the outer side of a body trunk supporter in accordance with Embodiment 1 of the present invention.
Figure 2:
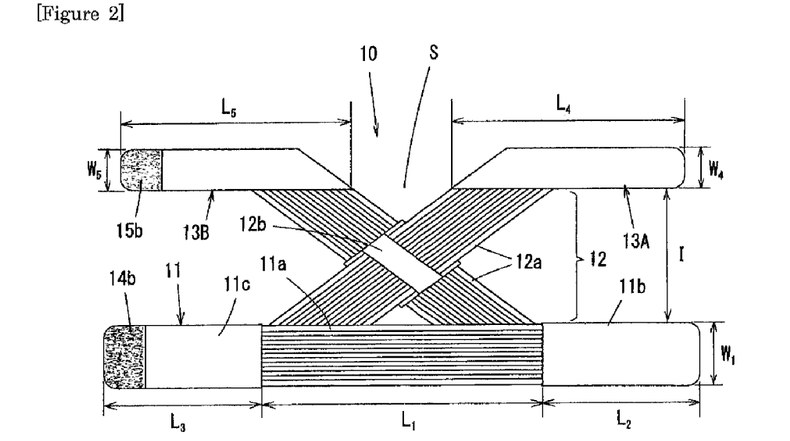
FIG. 2 illustrates the inner side of the body trunk supporter in accordance with Embodiment 1.
Figure 3:
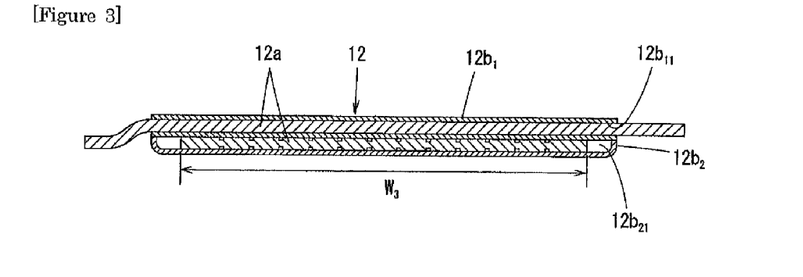
FIG. 3 illustrates an enlarged end view of a C-C portion taken from line A-A of FIG. 1.
Figure 4:
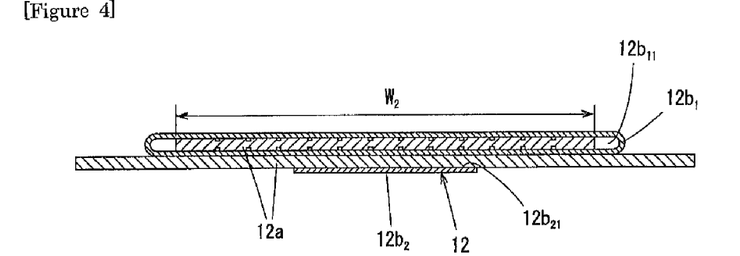
FIG. 4 illustrates an enlarged end view of the C-C portion taken from line B-B of FIG. 1.
Figure 5:
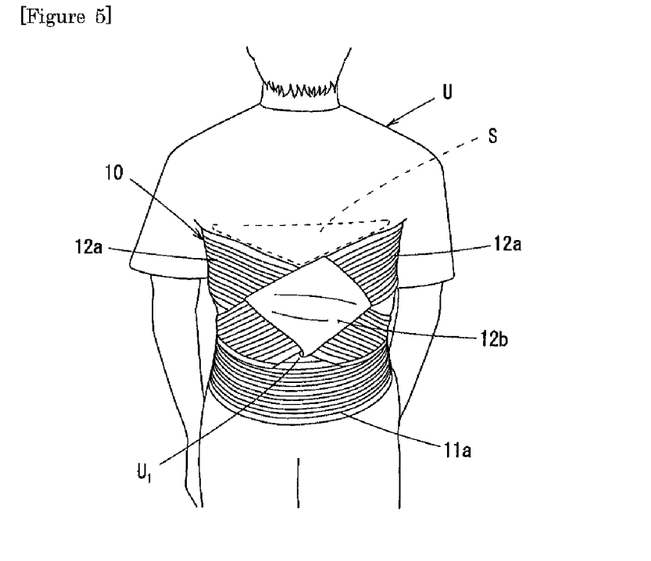
FIG. 5 illustrates the body trunk supporter in accordance with Embodiment 1 in a usage state viewed from the back.
Figure 6:
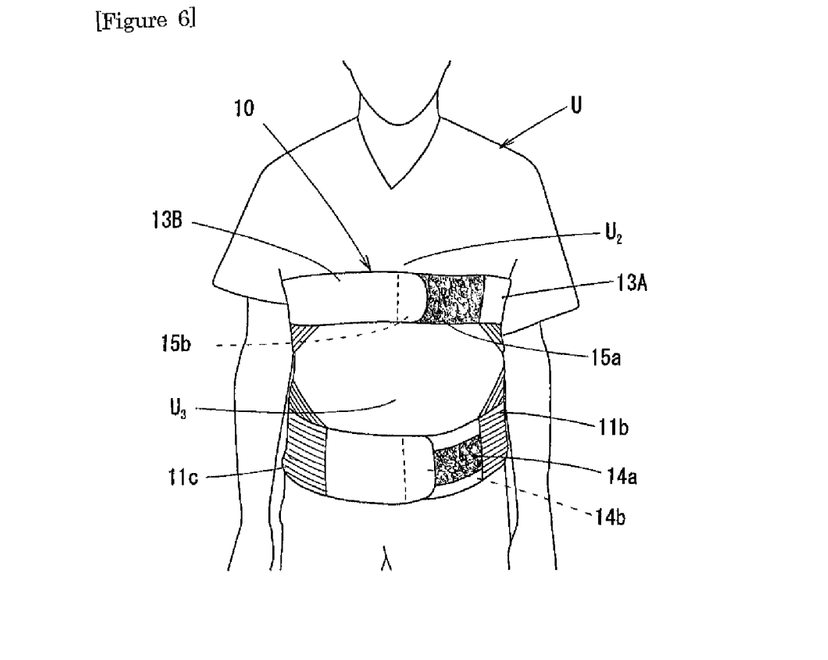
FIG. 6 illustrates the body trunk supporter in accordance with Embodiment 1 in a usage state viewed from the front.
Figure 7:
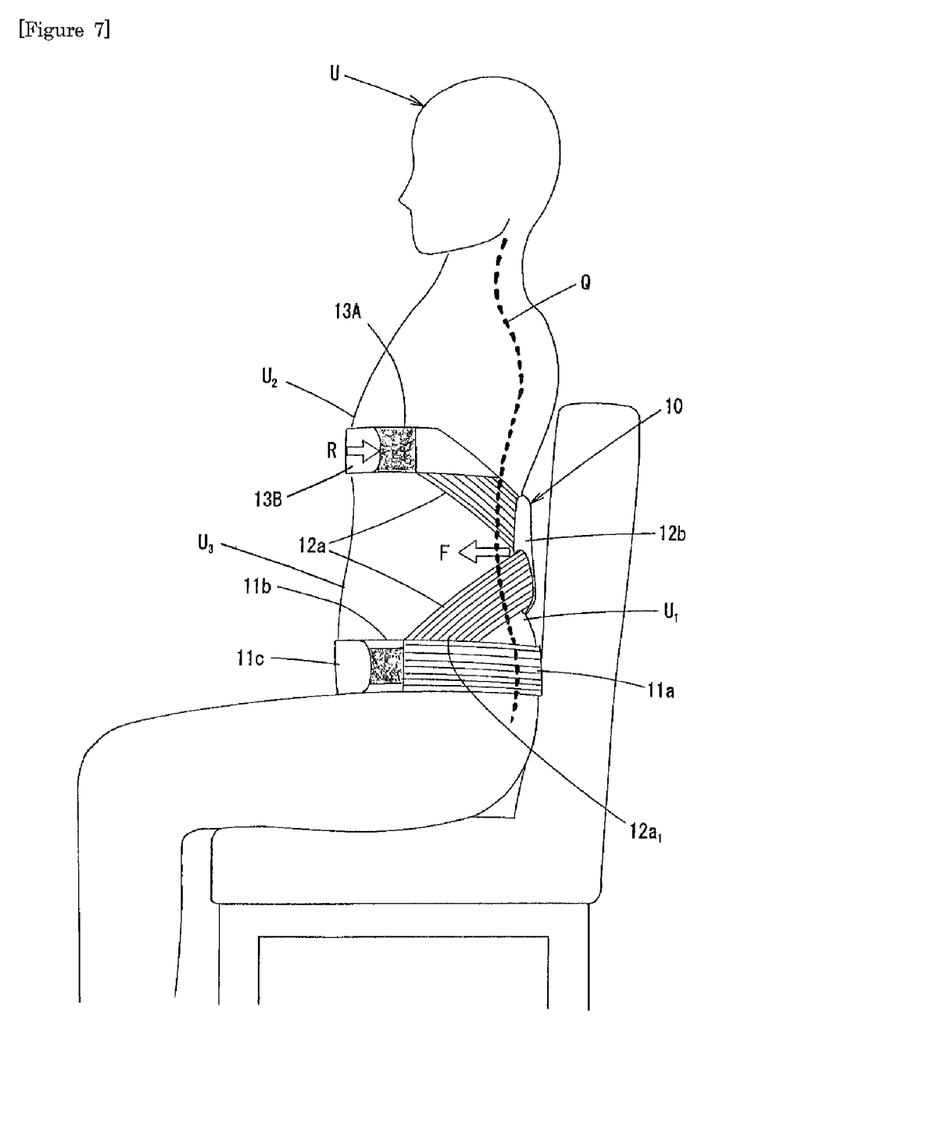
FIG. 7 illustrates the body trunk supporter in accordance with Embodiment 1 in a usage state in a sitting posture viewed from the left side.

FIG. 1 illustrates the outer side of a body trunk supporter in accordance with Embodiment 1 of the present invention; and FIG. 2 illustrates the inner side of the body trunk supporter in accordance with Embodiment 1. FIG. 3 illustrates an enlarged end view of a C-C portion taken from line A-A of FIG. 1; and FIG. 4 illustrates an enlarged end view of the C-C portion taken from line B-B of FIG. 1. FIG. 5 illustrates the body trunk supporter in accordance with Embodiment 1 in a usage state viewed from the back; and FIG. 6 illustrates the body trunk supporter in accordance with Embodiment 1 in a usage state viewed from the front; and FIG. 7 illustrates the body trunk supporter in accordance with Embodiment 1 in a usage state in a sitting posture viewed from the left side.

Structure of Body Trunk Supporter

As illustrated in FIGS. 1 to 4, a body trunk supporter 10 in accordance with Embodiment 1 comprises a belt-like (or girdle-like) and stretchable (or elastic) lower band section 11; an X-shaped and stretchable (or elastic) middle band section 12 having a pair of lower end parts $12a_1$ attached to the lower band section 11; and a pair of upper band sections 13A and 13B respectively attached to a pair of upper end parts $12a_2$ of the middle band section 12. Edges of the end parts $12a_1$ and edges of the other end parts $12a_2$ of the middle band section 12 extend in a direction parallel to a longitudinal direction of the lower band section 11.

The lower band section 11 is a section adapted to be wrapped around and positioned (or fastened) at the pelvis of a user U; and this section has a belt-like and stretchable rubber band section 11a and a pair of belt-like and non-stretchable cloth band sections 11b and 11c sewn to both ends of the rubber band section 11a in a longitudinal direction.

The lower band section 11 respectively has lower surface fastener portions at its ends.

One of the lower surface fastener portions has a lower loop fiber surface portion 14a sewn to the front (outer side) of the cloth band section 11b; and the other lower surface fastener portion has a lower hook fiber surface portion 14b sewn to the back (inner side) of the cloth band section 11c. In Embodiment 1, the lower loop fiber surface portion 14a is formed at one of the lower band sections and is designed to have the same length as a length of the cloth band section 11b; and the lower hook fiber surface portion 14b is formed at the other lower band section and is placed only at a tip portion of the cloth band section 11c.

The middle band section 12 is a section that is adapted to press areas of the lumbar region $U_1$ (lumbar area) of the user U; and the middle band section comprises the following components: a pair of rubber band members 12a having an intersection part of X shape; and a retention member 12b made of cloth, the retention member being provided at the intersection part of the pair of rubber band members 12a and having a pair of loop parts $12b_{11}$ and $12b_{21}$ through which the rubber band members 12a are respectively inserted (or pass).

The retention member 12b has a diamond-shaped tubular portion $12b_1$ at the front (outer side) with the loop part $12b_{11}$ through which one of the rubber band members 12a is inserted, and also has a narrow belt-like band loop part $12b_2$ sewn to an outer surface of the tubular portion $12b_1$ (i.e., the inner side of the supporter) in such a way as to form the loop part $12b_{21}$ through which the other rubber band member 12a is inserted. Since the retention member 12b is not sewn to the pair of rubber band members 12a, the pair of rubber band members 12a is freely movable from the retention member 12b. This retention member 12b may be knitted by means of three-dimensional honeycomb knitting.

The pair of upper band sections 13A and 13B are sections that are adapted to be wrapped around and positioned (or stabilized) at the chest $U_2$ of the user U, and are formed of non-stretchable cloth.

The upper band section 13A has a unilateral edge portion sewn to the end part 12b of the rubber band member 12a extending in parallel with the lower band section 11, and extends in the same direction as the cloth band section 11b on the lower loop fiber surface portion 14a side of the lower band section 11.

The upper band section 13B has a unilateral edge portion sewn to the end part 12b of the rubber band member 12a extending in parallel with the lower band section 11, and extends in the same direction as the cloth band section 11c on the lower hook fiber surface portion 14b side of the lower band section 11.

A distance I from the lower band section 11 to the pair of upper band sections 13A and 13B is the same.

As illustrated in FIGS. 1 and 2, the pair of upper band sections 13A and 13B are separated from each other and extend in opposite directions in an unfolded state. That is, there is an inverted triangular space S formed between the upper band section 13A and the upper band section 13B in the unfolded state.

The pair of upper band sections 13A and 13B respectively have upper surface fastener portions provided at their distal ends.

These upper surface fastener portions comprise the following components, respectively: an upper loop fiber surface portion 15a sewn to an outer surface of the upper band section 13A; and an upper hook fiber surface portion 15b sewn to an inner surface of the upper band section 13B. In Embodiment 1, the upper loop fiber surface portion 15a is configured to have a length approximately equal to half a length $L_4$ of the upper band section 13A; and the upper hook fiber surface portion 15b is formed only at the distal end of the upper band section 13B.

How to Wear Body Trunk Supporter

Through the use of FIGS. 1, 2 and 5 to 7, examples of how to wear the body trunk supporter 10 in accordance with Embodiment 1 will be described.

An example of how to wear the body trunk supporter 10 will be described below such that the inner side of the body trunk supporter that has a band loop part $12b_2$ of the retention member 12b comes in tight contact with the user U; however, the body trunk supporter may be worn such that the outer side of the body trunk supporter comes in tight contact with the user U.

Firstly, bring the body trunk supporter 10 on the back side of the user U; hold the cloth band section 11b of the lower band section 11 with the left hand, and hold the other cloth band section 11c with the right hand; place the rubber band section 11a on a lower part of the lumbar region $U_1$ while pulling the pair of cloth band sections 11b and 11c toward the front so as to wrap the cloth band sections around a lower part of the abdomen $U_3$ (lower abdomen); and overlap the lower hook fiber surface portion 14b on the lower loop fiber surface portion 14a. This allows the lower loop fiber surface portion 14a and the lower hook fiber surface portion 14b to be surface-contact fastened to each other; and the lower band section 11 is positioned (or becomes steady) around the user's pelvis.

Secondly, hold the upper band section 13A with the left hand, and hold the other upper band section 13B with the right hand; pull both the upper band sections 13A and 13b toward the front so that the upper band sections come under both arms, respectively, and are wrapped around the chest $U_2$; and overlap the upper hook fiber surface portion 15b on the upper loop fiber surface portion 15a. This allows the upper loop fiber surface portion 15a and the upper hook fiber surface portion 15b to be surface-contact fastened to each other; and the upper band sections 13A and 13B are positioned around the user's chest $U_2$, completing that the user is clothed in the body trunk supporter 10.

The pair of rubber band members 12a of the middle band section 12 of the above-described body trunk supporter 10 worn by the user pass near the fifth to the tenth ribs of the rib cage of the user U through the oblique muscles along the erector spinae muscles; and the pair of upper band sections 13A and 13B are fastened by surface-contact fastening at a front part of the rib cage. In this way, the upper band sections 13A and 13B and the lower band section 11 are respectively positioned at upper and lower positions of the abdomen $U_3$ of the user U; and the abdomen $U_3$ is not compressed (or squeezed) by the body trunk supporter 10.

Since a cross portion of the middle band section 12 (retention member 12b) is positioned near the lumbar region $U_1$ of the user U, the retention member 12b presses the areas of the lumbar region $U_1$ by an elastic force of the pair of rubber band members 12a.

More specifically, the pair of rubber band members 12a descends from the both sides of the user's body toward the cross portion; and lower ends of the rubber band members (a pair of lower end parts $12a_1$ of the middle band section 12) are joined to areas ranging from positions immediately lateral to the pelvis of the user U to their adjacent anterior positions in the lower band section 11a. The inverted triangular space S is formed above the cross portion of the middle band section 12.

As illustrated in FIG. 7, the body trunk supporter 10 designed as above is configured to press the lumbar vertebrae in the lumbar region $U_1$ forward (in a direction of the arrow F); and the pair of upper band sections 13A and 13B effectively presses the chest $U_2$ rearward (in a direction of the arrow R), with the result that the user U can maintain a good posture by expanding his/her chest naturally and straightening his/her back. That is, the muscular strength of the erector spinae muscles of the lumbar region $U_1$ of the user U is supported; and muscle tension is reduced; in addition to that, right and left distortions of the body are reformed; and the spinal column Q is kept in a normal S-shaped curve, bringing about a relieving effect and/or a preventive effect of low back pain.

Workers, such as desk workers and taxi or truck drivers in particular, who need to be seated and sustain their postures for a long time are likely to lose their postures and to strain their backs; however, these people (users U) can sustain their good sitting posture for a long time by wearing the body trunk supporter 10 of the present invention, leading to a reduction in burden on the lumbar region $U_1$.

The body trunk supporter 10 of the present invention can also be used by people who carry heavy loads, workers who work as leaning forward, and people who practice a sport requiring a torsion to hit a ball, such as golf, tennis, or baseball, because the body trunk supporter can support the user's waist muscles and reduce the burden on their back, and also helps to improve muscle performance.

Moreover, since the body trunk supporter 10 of the present invention does not squeeze the abdomen $U_3$ of the user, the user can eat or drink while wearing the body trunk supporter 10, and also can be free from worry about breathing problems, digestive system problems, cardiovascular problems, etc. that can occur by squeezing the abdomen $U_3$.

If the pair of lower end parts $12a_1$ of the middle band section 12 (the lower ends of the pair of rubber band members 12a) are connected with an area posterior to areas (on the back side) ranging from the positions immediately lateral to the pelvis of the user U to adjacent anterior positions thereof in the lower band section 11a, such a structure is not desirable because the entire middle band section 12 presses the back of the user U in a planar manner; and the pressing force of the cross portion against the lumbar vertebrae decreases.

Embodiment 2

Figure 8:
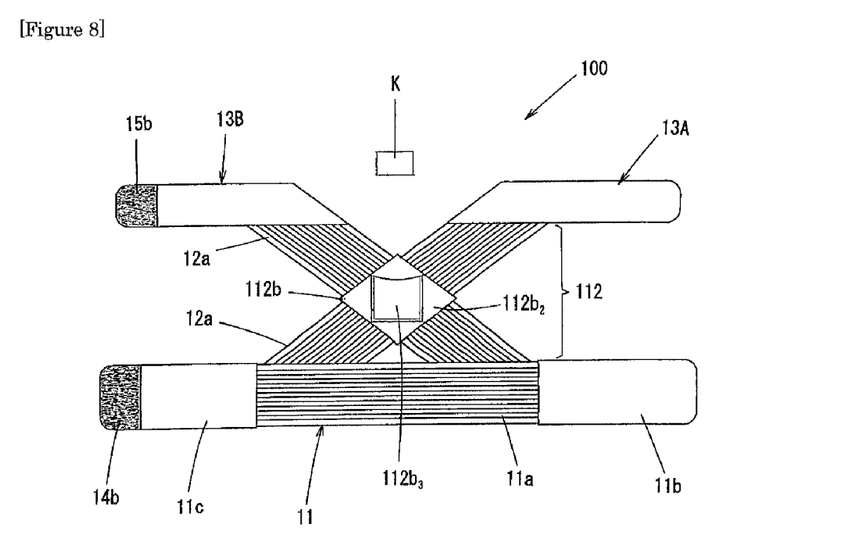
FIG. 8 illustrates the inner side of a body trunk supporter in accordance with Embodiment 2 of the present invention.

FIG. 8 illustrates the inner side of a body trunk supporter in accordance with Embodiment 2 of the present invention. The reference signs of the components used in FIG. 2 are used for components in FIG. 8.

A body trunk supporter 100 in accordance with Embodiment 2 is the same as the body trunk supporter 10 of Embodiment 1, except that a retention member 112b of a middle band section 112 is different in structure from the retention member 12b in accordance with Embodiment 1.

Hereinafter, a structure in accordance with Embodiment 2 will be mainly described that is different from the structure in accordance with Embodiment 1.

In the body trunk supporter 100 in accordance with Embodiment 2, the retention member 112b of the middle band section 112 has the following components: a tube part (not illustrated) similar to that of Embodiment 1; a wide belt-like band loop part 112$b_2$ provided on an outer surface of this tube part (i.e., on the inner side of the supporter); and a pocket 112$b_3$ provided on an outer surface of the band loop part 112$b_2$ (i.e., on the inner side of the supporter).

The pocket 112$b_3$ provided on an outer surface of the retention member 112b is a pocket in which a commercially available disposable body warmer K is put. This pocket 112$b_3$ may be knitted by means of three-dimensional honeycomb knitting.

The structure designed as above can have the pocket 112$b_3$ that is capable of keeping the disposable body warmer K inside and of allowing the disposable body warmer K to warm the back area of the user who wears the body trunk supporter 110 due to the heat-producing disposable body warmer K in such a way that the pocket 112$b_3$ side touches the user's body. As a result, this structure is capable of promoting blood circulation near the lumbar area of the user, and lessening or preventing the user's back pain more effectively.

At the retention member 112b, the pocket 112$b_3$ may be placed on the outer surface of the tube part (i.e., on the outer side of the supporter); and in this case, the user may wear the body trunk supporter in such a way that the outer side of the retention member 112b comes in close contact with the user.

Embodiment 3

Figure 9A:
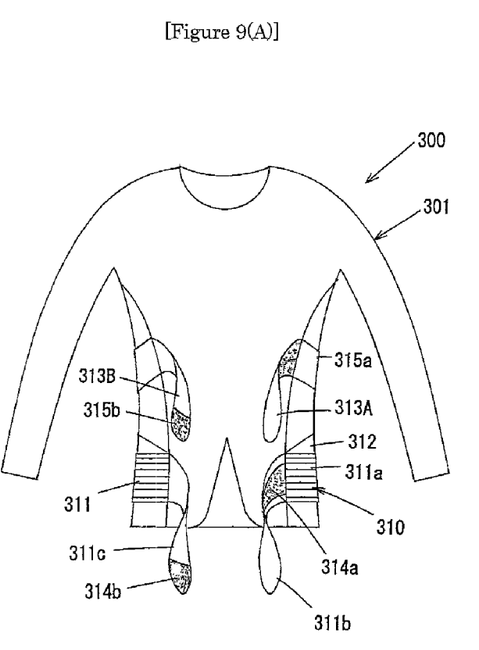
FIG. 9(A) illustrates a wear viewed from the front that is provided with a body trunk supporter in accordance with Embodiment 3 of the present invention.
Figure 9B:
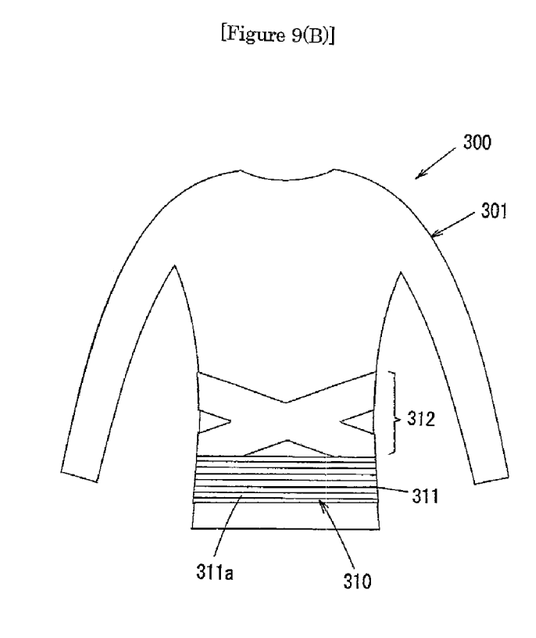
FIG. 9(B) illustrates the wear viewed from the back.

FIG. 9(A) illustrates a wear viewed from the front that is provided with a body trunk supporter in accordance with Embodiment 3 of the present invention; and FIG. 9(B) illustrates the wear viewed from the back.

A wear 300 comprises a wear body 301 and a body trunk supporter 310 provided on an outer surface of the wear body 301. In Embodiment 3, the wear 300 is exemplified as long-sleeved underclothing, but may be short-sleeved underclothing. The "underclothing" here also includes any clothing that may be worn between an undershirt and an outer wear.

The wear body 301 may be sports underclothing made of, for example, elastic fabrics.

The body trunk supporter 310 comprises a lower band section 311; an X-shaped elastic middle band section 312; and a pair of upper band sections 313A and 313B; and this body trunk supporter may have the same structure as that of the body trunk supporter 10 described in Embodiment 1. It is desirable that the body trunk supporter 310 is thinly made because this supporter is sewn to an outer surface of the wear body 301.

In the same way as the body trunk supporter 10 of Embodiment 1 that is adapted to be positioned at the different parts of the user's body, the body trunk supporter 310 of Embodiment 3 is sewn to the wear body 301 so that the supporter is positioned at different parts of the body of a user who wears the wear 300. The following two pairs of band sections, however, are not sewn to the wear body 301: a pair of cloth band sections 311b and 3311c at both ends of a rubber band section 311a of the lower band section 311; and a pair of upper band sections 313A and 313B.

In a similar way to Embodiment 1, the cloth band section 311b and the upper band section 313A respectively have, on their front surfaces, loop fiber surface portions 314a and 315a of hook-and-loop fasteners; and the other cloth band section 311c and the other upper band section 313B respectively have, on their back surfaces, hook fiber surface portions 314b and 315b of the hook-and-loop fasteners.

The middle band section 312 may be formed by crossing a pair of rubber band sections as in Embodiment 1; however, the middle band section in accordance with Embodiment 3 is formed by cutting out or sewing thin fabric (stretch fabric) in an X-shaped configuration that is stretchable in two directions so as not to make the fabric overlapped. Alternatively, rubber bands may be sewn in an X-shaped configuration. The retention member provided in the middle band section of Embodiment 1 is omitted in Embodiment 3.

In this way, a cross portion of the middle band section 312 does not become bulky; therefore, this makes it possible for the user to wear clothes over the wear 300 without any discomfort; in addition, the clothes do not become bulky at the cross portion and do not look bulgy.

The wear 300 in accordance with Embodiment 3 configured as described above can be positioned in the following order: The pair of cloth band sections 311b and 311c of the lower band section 311 are overlapped with each other at a front portion of the pelvis of the user and are positioned by surface-contact fastening with use of the hook-and-loop fastener; the pair of upper band sections 313A and 313B are wrapped around fifth to tenth ribs of the user's chest and are overlapped with each other at a front portion of the chest; and the upper band sections are positioned by surface-contact fastening with use of the hook-and-loop fastener. Namely, the body trunk supporter 310 can be worn in the same way as the body trunk supporter of Embodiment 1, achieving the same effects as in Embodiment 1.

The body trunk supporter 310 can be hidden by wearing clothing such as a T-shirt or a dress shirt on the wear 300; therefore, the user can perform sports and everyday activities without caring someone's eyes (or being bothered by other people's attention) while wearing the body trunk supporter 310.

The body trunk supporter 310 may be detachably attached to the wear body 301 with use of hook-and-loop fasteners (planar fasteners). In this way, the body trunk supporter 310 can be detached from the wear body 301; and only the wear body 301 that may be easy to get dirty (or is likely to be soiled) can be washed.

Modified Example of Embodiment 3

The wear body 301 of the wear 300 described through the use of FIGS. 9(A) and 9(B) may be outerwear.

Embodiment 4

Figure 10A:
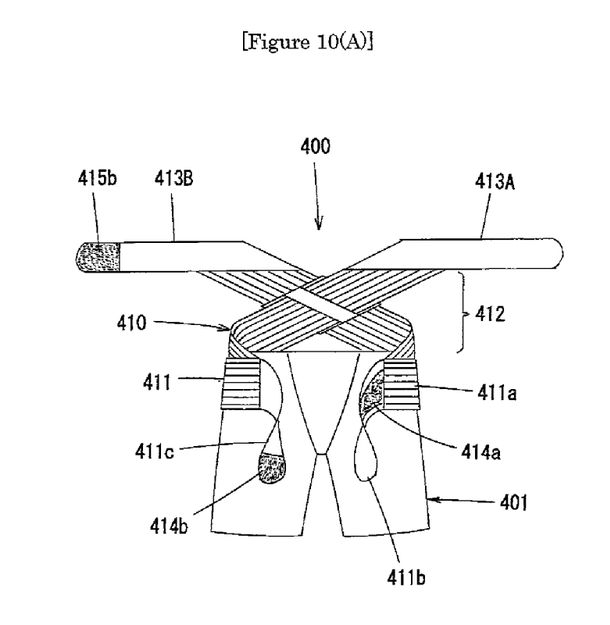
FIG. 10(A) illustrates a wear viewed from the front that is provided with a body trunk supporter in accordance with Embodiment 4 of the present invention.
Figure 10B:
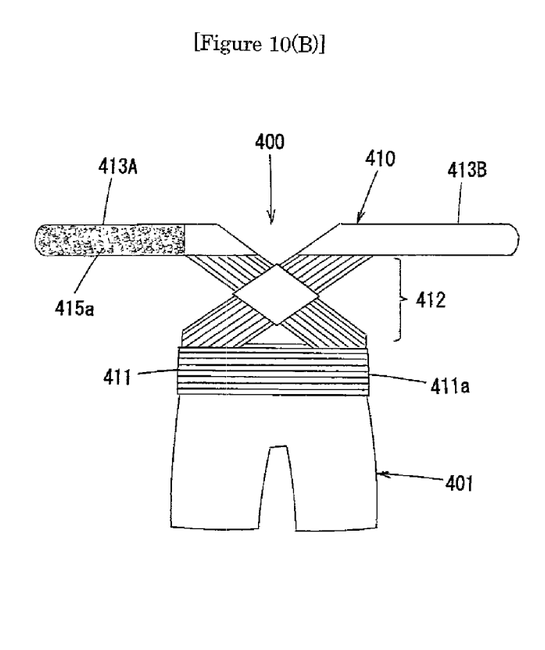
FIG. 10(B) illustrates the wear viewed from the back.

FIG. 10(A) illustrates a wear viewed from the front that is provided with a body trunk supporter in accordance with Embodiment 4 of the present invention; and FIG. 10(B) illustrates the wear viewed from the back.

A wear 400 in accordance with Embodiment 4 is formed by sewing a body trunk supporter 410 to an outer surface of a pants-type wear body 401 so as to integrate the supporter with the wear body. Embodiment 4 exemplifies shorts-type sports tights as the wear 400; however, the wear may be long pants-type sports tights or underclothing such as briefs, boxer shorts, trunks, and high-waisted type. The "underclothing" here also includes any clothing that can be worn between an undershirt and an outer wear.

The body trunk supporter 410 comprises the following components: a lower band section 411; an X-shaped stretchable middle band section 412; and a pair of upper band sections 413A and 413B; and this body trunk supporter may have the same structure as that of the body trunk supporter 10 described in Embodiment 1.

In Embodiment 4, a rubber band section 411*a* of the lower band section 411 of the body trunk supporter 410 is sewn from a back surface of a waist area of the wear body 401 to right-and-left side surfaces; and other sections than the rubber band section 411*a* of the body trunk supporter 410 are not sewn to the wear body 401.

In the same way as in Embodiment 1, loop fiber surface portions 414*a* and 415*a* of hook-and-loop fasteners are provided, respectively, on front surfaces of a cloth band section 411*b* of the lower band section 411 and an upper band section 413A; and hook fiber surface portions 414*b* and 415*b* of the hook-and-loop fasteners are provided, respectively, on back surfaces of other cloth band section 411*c* and other upper band section 413B.

The middle band section 412 may be formed, in the same way as in Embodiment 1, by crossing a pair of rubber band sections; however, the middle band section may be formed, as in Embodiment 3, by cutting out or sewing thin fabric (stretch fabric) in an X-shaped configuration that is stretchable in two directions so as not to make the fabric overlapped, or by sewing rubber bands in an X-shaped configuration.

A user wearing an undershirt can wear the body trunk supporter 410 as follows: The user wears the wear body 401; the pair of cloth band sections 411*b* and 411*c* are overlapped with each other on the abdominal side and are positioned by surface-contact fastening with use of the hook-and-loop fastener; and the pair of upper band sections 413A and 413B on the back side are wrapped around the rib cage (near fifth to tenth ribs of the user's chest) over the undershirt, and are overlapped with each other so as to position the upper band sections with use of the hook-and-loop fastener, achieving the same effects as in Embodiment 1.

The body trunk supporter 410 in accordance with Embodiment 4 can be hidden by wearing clothing such as a T-shirt or a dress shirt thereon; therefore, the user can perform sports and everyday activities without caring someone's eyes while wearing the body trunk supporter 410.

The body trunk supporter 410 may be detachably attached to the wear body 401 with use of planar fasteners. In this way, the body trunk supporter 410 can be detached from the wear body 401; and only the wear body 401 that may be easy to get dirty can be washed.

Modified Example of Embodiment 4

The wear body 401 of the wear 400 described through the use of FIGS. 10(A) and 10(B) may be outerwear such as half pants-type, long pants-type, or high-waisted pants-type. In this case, the body trunk supporter serves also as a belt that prevents the outerwear from sliding down.

Embodiment 5

Figure 11A:
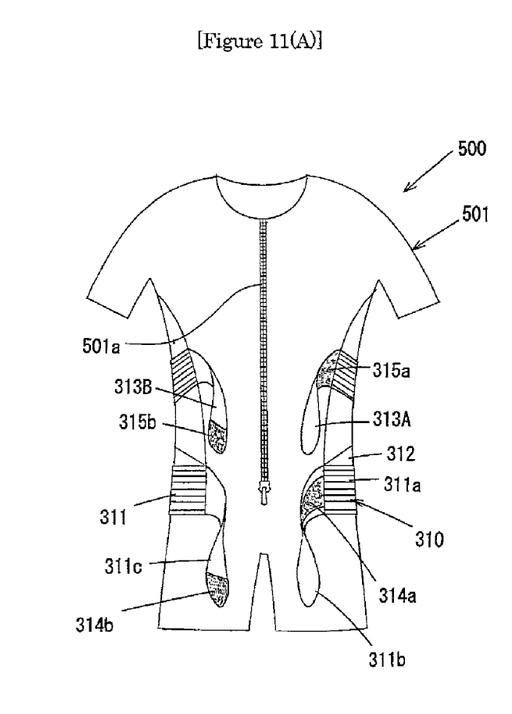
FIG. 11(A) illustrates a wear viewed from the front that is provided with a body trunk supporter in accordance with Embodiment 5 of the present invention.
Figure 11B:
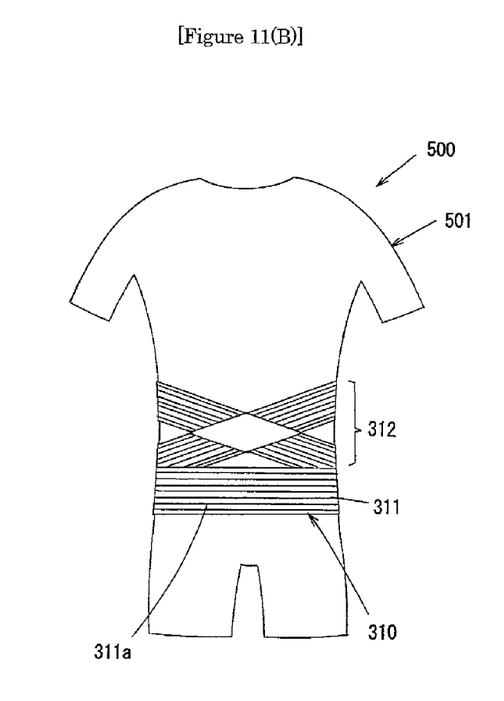
FIG. 11(B) illustrates the wear viewed from the back.

FIG. 11(A) illustrates a front view of a wear provided with a body trunk supporter in accordance with Embodiment 5 of the present invention; and FIG. 11(B) illustrates a rear view thereof. The reference signs of the components used in FIGS. 9(A) and 9(B) are used for components in FIGS. 11(A) and 11(B).

A wear 500 in accordance with Embodiment 5 is formed by sewing a body trunk supporter 510 to an outer surface of a body tights-type (or a body suit-type) wear body 501 provided with a fastener part 501*a* from the chest to the abdomen so as to integrate the supporter with the wear body. Embodiment 4 exemplifies, as the wear 500, body tights-type undershirt having short sleeves and half pants; however, the wear may be underclothing such as a body tights type having long sleeves and long pants or a leotard type. The "underclothing" here includes any clothing that can be worn between an undershirt and an outer wear.

Modified Example of Embodiment 5

The wear body 501 of the wear 500 described through the use of FIGS. 11(A) and 11(B) may be outerwear.

Embodiment 6

The inner wear 300 provided with the body trunk supporter 310 illustrated in FIG. 9 (Embodiment 3) may be provided with a pocket in which a disposable body warmer can be placed on the cross portion of the middle band section 312, in the same way as Embodiment 2.

The inner wear 300 provided with the body trunk supporter 310 illustrated in FIG. 9 may not have a portion where touches a lower back portion of the lower band section 311—i.e., an area between a pair of lower ends of the middle band section 312—and such a structure can still achieve the same effects as in Embodiment 3.

The same applies to the structure in accordance with FIG. 10 (Embodiment 4 and its Modified Example) and the structure in accordance with FIG. 11 (Embodiment 5 and its Modified Example).

Embodiment 7

Embodiments 1 to 5 exemplify that the lower band section of the body trunk supporter has the stretchability (elasticity); however, the lower band section may be formed of fabric having no stretchability (elasticity).

Embodiment 8

Embodiments 1, 2, 4 and 5 exemplify that the middle band section of the body trunk supporter has the retention member; however, the retention member may be omitted. In this case, the pair of rubber band members may be sewn together, for example, at their central part so that the pair of rubber band members do not separate.

Embodiment 9

Figure 12A:
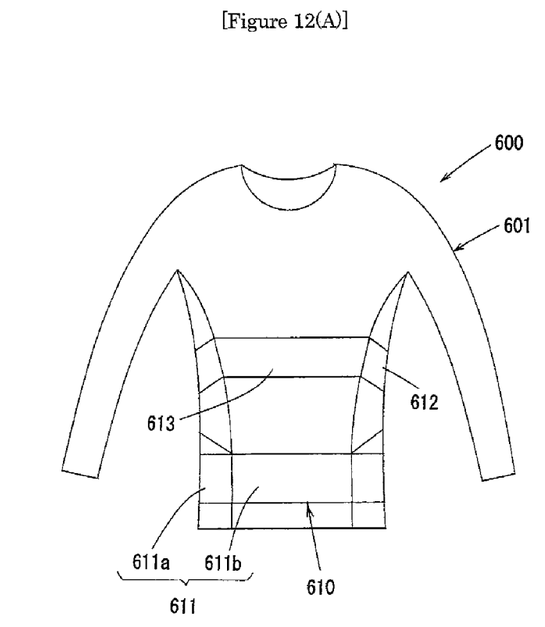
FIG. 12(A) illustrates a wear viewed from the front that is provided with a body trunk supporter in accordance with Embodiment 9 of the present invention.
Figure 12B:
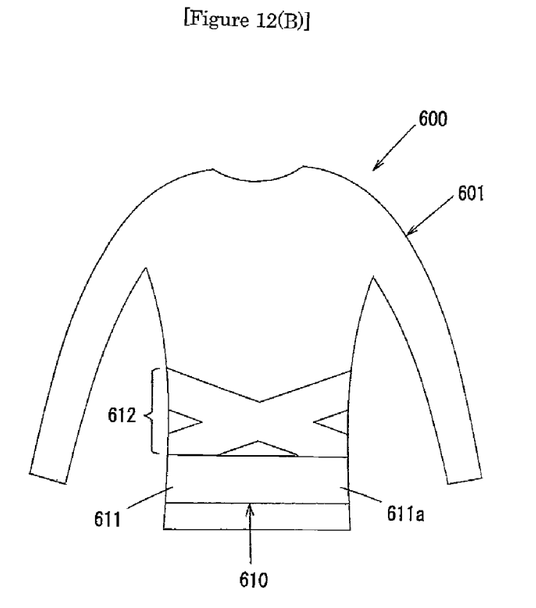
FIG. 12(B) illustrates the wear viewed from the back.

FIG. 12(A) illustrates a front view of a wear provided with a body trunk supporter in accordance with Embodiment 9 of the present invention; and FIG. 12 (B) illustrates a rear view thereof.

Embodiment 3 (FIGS. 9(A) and 9(B)) and Embodiment 5 (FIGS. 11(A) and 11(B)) each exemplify that the body trunk supporter is partially sewn to the outer surface of the wear body; however, as in a wear 600 illustrated in FIGS. 12(A) and 12(B) in accordance with Embodiment 9, a body trunk supporter 610 may be provided on a wear body 601. In FIGS. 12(A) and 12(B), long-sleeved underclothes are exemplified; however, the wear may be underclothes with short sleeves or may be body tights-type underclothes.

The wear 600 in accordance with Embodiment 9 comprises the wear body 601 and the body trunk supporter portion 610 provided on the wear body 601, wherein the body trunk supporter portion 610 comprises the following components: a belt-like lower band section 611 placed so as to be wrapped around the pelvis of a user; an X-shaped stretchable middle band section 612 that has a pair of lower end parts joined to the lower band section 611 and presses areas of the lumbar region of the user; and an upper band section 613 that has both ends joined to a pair of upper end parts of the middle band section 612 and that is positioned so as to be wrapped around the chest of the user;

the pair of lower end parts of the middle band section 612 are connected with areas ranging from positions immediately lateral to the pelvis of the user to adjacent anterior positions thereof in the lower band section 611; and the upper band section 613 is configured to be placed near fifth to tenth ribs of the chest of the user.

More specifically, the entire body trunk supporter 610 in accordance with Embodiment 9 may be sewn to an outer surface of the wear body 601 (Embodiment 9-1) or may be pasted thereto (Embodiment 9-2) or may be knitted thereinto (Embodiment 9-3).

Embodiment 9-1

In this case, the body trunk supporter 610 may be made of the same material as that of the body trunk supporter 10 described in Embodiment 1; and the body trunk supporter having the following structure may be sewn to the outer surface of the elastic wear body 601.

Firstly, for example, a rubber band section 611a of the lower band section 611 and the middle band section 612 made of a rubber band are sewn to the wear body 601; and lower ends of the X-shaped middle band section 612 are sewn to and connected with an upper edge of the rubber band section 611a.

Then, a cloth band section 611b of the lower band section 611 is sewn to the wear body 601; and both ends of the cloth band section 611b are respectively sewn to and connected with both ends of the rubber band section 611a.

The upper band section 613 made of cloth is sewn to the wear body 601; and both ends of the upper band section 613 are respectively sewn to and connected with upper ends of the X-shaped middle band section 612.

The order of the sewing of the body trunk supporter is not limited to the above.

Alternatively, the body trunk supporter 610 made of knit material may be sewn to the outer surface of the wear body 601. In this case, the following two portions may be formed by high-stretch knitting: the portion comparable to the rubber band section 611a of the lower band section 611 of the body trunk supporter 610; and the portion comparable to the middle band section 612; and the following two portions may be formed by low-stretch knitting: the portion comparable to the cloth band section 611b of the lower band section 611; and the portion comparable to the upper band section 613.

Embodiment 9-2

In this case, for example, the following two portions each of the lower band section 611 are formed of a urethane sheet: the portion comparable to the rubber band section 611a; and the portion comparable to the cloth band section 611b; and the following two portions each are formed of a urethane sheet: the portion comparable to the middle band section 612; and the portion comparable to the upper band section 613, all the portions constituting the body trunk supporter 610 and being adhered to the outer surface of the wear body 601 by thermal fusion in order.

In this case, for example, the portion comparable to the rubber band section 611a of the lower band section 611 and the portion comparable to the middle band section 612 each may be formed of the urethane sheet that is high in stretchability (elasticity); and the portion comparable to the cloth band section 611b of the lower band section 611 and the portion comparable to the upper band section 613 each may be formed of the urethane sheet that is low in stretchability.

Alternatively, the body trunk supporter 610 may be formed on the outer surface of the wear body 601 by forming coating films at the following portions constituting the body trunk supporter 610 with use of a printing technique (for example, screen printing) and drying the films: the portion comparable to the rubber band section 611a and the portion comparable to the cloth band section 611b of the lower band section 611; and the portion comparable to the middle band section 612 and the portion comparable to the upper band section 613, the films containing a urethane-based resin, a silicon-based resin, an acrylic resin, rubber, or the like.

In this case, for example, the portion comparable to the rubber band section 611a of the lower band section 611 and the portion comparable to the middle band section 612 may be formed of the coating films that are high in stretchability; and the portion comparable to the cloth band section 611b of the lower band section 611 and the portion comparable to the upper band section 613 may be formed of the coating films that are low in stretchability.

Embodiment 9-3

In this case, for example, the wear body 601 made of the knit material is formed by knitting the body trunk supporter 610 into the wear body 601. At this time, the following portions may be knitted so as to be higher in stretchability (elasticity) than the wear body 610: the portion comparable to the rubber band section 611a of the lower band section 611 and the portion comparable to the middle band section 612; and the following potions may be knitted so as to be lower in stretchability than the wear body 610: the portion comparable to the cloth band section 611b of the lower band section 611 and the portion comparable to the upper band section 613.

Conclusions

The present invention relates to the body trunk supporter for correcting the spinal column to a normal S-shaped curve and for alleviating or preventing low back pain by wearing the supporter on a human torso (body trunk). As illustrated in FIG. 1, the present invention has the following features: The X-shaped middle band section 12 having the pair of lower end parts is joined to the belt-like lower band section 11; the edges of the one end parts and the edges of the other end parts of the middle band section 12 extend in the direction parallel to the direction of the lower band section 11; and the edges are respectively joined to the pair of upper band sections 13A and 13B having the hook-and-loop fasteners.

As illustrated in FIGS. 5 and 6, the lower band section 11 is configured to be wrapped around the areas ranging from the positions immediately lateral to the pelvis to adjacent anterior positions thereof; the pair of upper band sections 13A and 13B are configured to be wrapped around fifth to tenth ribs of the chest $U_2$, and are respectively positioned by use of the hook-and-loop fasteners; and the middle band section 12 in the shape of the letter X is placed from the lower part of the right anterior chest to the left anterior pelvis and from the lower part of the left anterior chest to the right anterior pelvis of the user U. This enables the cross portion of the X-shaped middle band section 12 to be positioned at the area of the lumbar vertebrae of the user U and to support the erector spinae muscles of the lumbar region $U_1$, so that the muscle tension of the lumbar region $U_1$ can be eased; and the right and left contortions of the body can be corrected.

The cross portion of the X-shaped middle band section 12 pushes the lumbar vertebrae in the lumbar region $U_1$ forward; and the chest $U_2$ is drawn backward by the pair of upper band sections 13A and 13B, whereby the spinal column is corrected to become the correct S-shaped curve; and the back pain can be relieved (or reduced) or prevented. In this case, if the pair of upper band sections 13A and 13B are connected to each other on the back side, the force pulling the chest $U_2$ backward by the pair of upper band sections 13A and 13B decreases whereby it is difficult that the spinal column is corrected to be the normal S-shaped curve; however, the present invention is configured such that the pair of upper band sections 13A and 13B can be separated from each other in the deployed state and extend in the bilaterally opposite directions to each other; and the upper band sections also can be wrapped around and fastened near fifth to tenth ribs of the chest $U_2$ of the user U so that the present invention is capable of effectively correcting the spinal column to the correct S-shaped curve by interacting with the X-shaped middle band section 12.

In addition, the present invention (the body trunk supporter) does not compress the abdomen $U_3$ of the user U when being worn by the user, and thus has, for example, the following advantages: Various adverse effects involved with abdominal compression are not likely to arise in the human body, such as respiratory distress (breathing difficulty), gastrointestinal discomfort (digesting difficulty), and cardiovascular problems (cardiovascular dysfunction); the user can eat or drink while wearing the present invention without experiencing any discomfort in the abdomen $U_3$; and the present invention allows the user to carry out desk work comfortably in a sitting posture or to easily practice mild bending exercise, with the result that the present invention can be safely and comfortably used in daily life.

The disclosed Embodiments should be recognized as exemplifications in all respects and should not be recognized as limitative. The scope of the present invention is not described by the expositions above but is described in claims; and the scope of the present invention is intended to include the meanings (or the contents) equivalent to the scope of the claims and also include all alterations (and modifications) within the claims.

INDUSTRIAL APPLICABILITY

The body trunk supporter of the present invention is suitable for people who have expectations of alleviating low back pain, preventing low back pain, and/or correcting their postures.

REFERENCE SIGNS LIST 10, 100, 310, 410, 610 body trunk supporter (body core supporter)
11, 311, 411, 611 lower band section
12, 112, 312, 412, 612 middle band section
12a, 312a rubber band member
$12a_1$ one end parts
$12a_2$ other end parts
12b, 112b retention member
$12b_1$ tube part
$12b_{11}$, 12b loop part
$12b_2$, $112b_2$ band loop part
13A, 13B, 313A, 313B, 413A, 413B, 613 upper band sections
14a, 314a lower loop fiber surface portion
14b, 314b lower hook fiber surface portion
15a, 315a loop fiber surface portion
15b, 315b upper hook fiber surface portion
$112b_3$ pocket
300, 400, 500, 600 wear
301, 401, 501, 601 wear body
U user
$U_1$ lumbar region
$U_2$ chest

The invention claimed is:

1. A body trunk supporter provided with: one belt-like lower band section that is adapted to be wrapped around and positioned at the pelvis of a user; an X-shaped stretchable middle band section that has a pair of lower end parts joined to the lower band section and that is adapted to press areas of the lumbar region of the user; and a pair of upper band sections that are joined to a pair of upper end parts of the middle band section and that are adapted to be wrapped around and positioned at the chest of the user;
   wherein the pair of lower end parts of the middle band section are configured to be joined to areas ranging from positions that are immediately lateral to the pelvis of the user to adjacent anterior positions thereof in the lower band section;
   wherein the pair of upper band sections are configured to be separated from each other and to extend in bilaterally opposite directions in an unfolded state, and are configured to be wrapped around and positioned near fifth to tenth ribs of the chest of the user; and
   wherein the pair of upper band sections and the lower band section are configured to be separated from each other at upper and lower positions so that the abdomen of the user is not compressed.

2. The body trunk supporter according to claim 1, wherein the lower band section has: a lower loop fiber surface portion of a lower surface fastener portion that is provided at one end of the lower band section; and a lower hook fiber surface portion of a lower surface fastener portion that is provided at the other end of the lower band section and that is connectable with the lower loop fiber surface portion by way of surface contact;
   one of the pair of upper band sections has an upper loop fiber surface portion of an upper surface fastener portion provided at one end of the upper band section; and
   the other one of the pair of upper band sections has an upper hook fiber surface portion of an upper surface fastener portion that is provided at the other end of the upper band section and that is connectable with the upper loop fiber surface portion by way of surface contact.

3. The body trunk supporter according to claim 1, wherein the lower band section has stretchability.

4. The body trunk supporter according to claim 1, wherein the middle band section is provided with: a pair of rubber band members having an intersection part of X shape; and a cloth retention member provided at the intersection part of the pair of rubber band members and having a pair of loop parts through which the rubber band members are respectively inserted.

5. The body trunk supporter according to claim 4, wherein the retention member has: a tube part having one of the loop parts through which one of the pair of rubber band members is inserted; a band loop part provided on an outer surface of the tube part and having the other of the loop parts through which the other of the pair of rubber band members is inserted; and a pocket provided on an outer surface of the tube part or on an outer surface of the band loop part.

6. A wear provided with: a wear body; and the body trunk supporter according to claim 1 provided on an outer surface of the wear body.

7. A wear provided with a wear body and a body trunk supporter provided on the wear body,
wherein the body trunk supporter is provided with: one belt-like lower band section that is adapted to be wrapped around and positioned at the pelvis of a user; an X-shaped stretchable middle band section that has a pair of lower end parts joined to the lower band section and that is adapted to press areas of the lumbar region of the user; and upper band sections that respectively have both ends joined to a pair of upper end parts of the middle band section and that are adapted to be wrapped around and positioned at the chest of the user;
wherein the pair of lower end parts of the middle band section are configured to be joined to areas ranging from positions that are immediately lateral to the pelvis of the user to adjacent anterior positions thereof in the lower band section;
wherein the upper band sections are configured to be positioned near fifth to tenth ribs of the chest of the user; and
wherein the pair of upper band sections and the lower band section are configured to be separated from each other at upper and lower positions so that the abdomen of the user is not compressed.

\* \* \* \* \*